United States Patent
Cahoon et al.

(12) 
(10) Patent No.: US 6,403,859 B1
(45) Date of Patent: Jun. 11, 2002

(54) VITAMIN B METABOLISM PROTEINS

(75) Inventors: Rebecca E. Cahoon, Wilmington; Saverio Carl Falco, Arden; J. Antoni Rafalski, Wilmington, all of DE (US)

(73) Assignee: E. I. du Pont de Nemours and Company, Wilmington, DE (US)

(*) Notice: Subject to any disclaimer, the term of this patent is extended or adjusted under 35 U.S.C. 154(b) by 0 days.

(21) Appl. No.: 09/371,056

(22) Filed: Aug. 9, 1999

Related U.S. Application Data

(60) Provisional application No. 60/096,342, filed on Aug. 12, 1998.
(51) Int. Cl.$^7$ .............................. A01H 1/00; C12N 9/12; C12N 5/14
(52) U.S. Cl. .................... 800/278; 435/6; 435/183; 435/194; 435/410; 435/419; 435/320.1; 435/252.1; 435/252.3; 435/254.2; 536/23.1; 536/23.2; 536/23.6; 800/295
(58) Field of Search ................ 435/183.6, 194, 435/252 B, 410, 419, 320.1, 252.1, 254.2; 536/23.1, 23.6, 23.2; 800/278, 295

(56) References Cited

PUBLICATIONS

Sasaki et al., Rice cDNA from callus 1995, Genbank Accession No. D39176, Nov. 1994.*

Minobe et al., Rice cDNA from Root, Genbank Accession No. D23776, Nov. 1993.*

Yong Yang et al., (1998), J. Bacteriol. 180:1814–1821, Identification and Function of the pdxY Gene, which encodes a novel Pyridoxal Kinase involved in the salvage pathway of Pyridoxal 5'–Phosphate Biosynthesis in *Escherichia coli* K–12.

Hon–Ming Lam et al., (1992), J. Bacteriol., 174:6033–6045, Characterization of the complex pdxH–tyrS Operon of *Escherichia coli* K–12 and Pleitropic Phenotypes caused by pdxH Insertion Mutations.

Genshi Zhao et al., (1995), J. Bacteriol. 177:883–891, Kinetic limitation and cellular amount of Pyridoxine (Pyridoxamine) 5'–Phosphate Oxidase of *Escherichia coli* K–12.

Adil Loubbardi et al., J. Bacteriol., 177(7):1817–1823, 1995, Sterol uptake induced by an Impairment of Pyridoxal Phosphate synthase in *Saccharomyces cerevisiae*: Cloning and Sequencing of the PDX3 gene encoding Pyridoxine (Pyridoxamine) Phosphate Oxidase.

National Center For Biotechnology Information General Identifier No. 2773404, Jan. 16, 1998, Z. G. Gao et al., Porcine Pyridoxal. cDNA cloning, expression and primary sequence conformation.

National Center For Biotechnology Information General Identifier No. 4505701, Mar. 19, 1999, M. C. Hanna et al., Human Pyridoxal Kinase. cDNA cloning, expression and modulation by ligands of the benzodiazepine receptor.

National Center For Biotechnology Information General Identifier No. 3122599, Jul. 15, 1998, T. Kaneko et al., Sequence analysis of the genome of the unicellular cyanobacterium Synechocystis sp. strain PCC6803. II. Sequence determination of the entire genome and assignment of potential protein–coding regions.

Takakazu Kaneko et al., DNA Res. 3 (3), 109–136, 1996, Sequence analysis of the genome of the unicellular cyanobacterium Synechocystis sp. strain PCC6803. II. Sequence determination of the entire genome and assignment of potential protein–coding regions.

National Center For Biotechnology Information General Identifier No. 3979940, Dec. 18, 1998, R. Wilson et al., 2.2 Mb of contiguous nucleotide sequence from chromosome III of C. elegans.

R. Wilson et al., Nature 368 (6466), 32–38 (1994), 2.2 Mb of contiguous nucleotide sequence from chromosome III of C. elegans.

National Center For Biotechnology Information General Identifier No. 3237304, Jun. 18, 1998, E. O. NGO et al.

Alfred H. Merrill et al., (1986), Methods Enzymol., 122:110–116, Highly sensitive methods for assaying the enzymes of vitamin B6 metabolism.

* cited by examiner

*Primary Examiner*—Rebecca E. Prouty
*Assistant Examiner*—Richard Hutson

(57) ABSTRACT

This invention relates to an isolated nucleic acid fragment encoding a vitamin B6 metabolic enzyme. The invention also relates to the construction of a chimeric gene encoding all or a portion of the vitamin B6 metabolic enzyme, in sense or antisense orientation, wherein expression of the chimeric gene results in production of altered levels of the vitamin B6 metabolic enzyme in a transformed host cell.

16 Claims, No Drawings

SEQUENCE LISTING

<160> NUMBER OF SEQ ID NOS: 16

<210> SEQ ID NO 1
<211> LENGTH: 933
<212> TYPE: DNA
<213> ORGANISM: Zea mays

<400> SEQUENCE: 1

| | | | | | |
|---|---|---|---|---|---|
| atggcgcggc | cgccgatcct | atccgtcgcg | ctgccgtctg | acaccggccg | tgtgctcagc | 60 |
| atccagtccc | acaccgtcca | ggggtatgtt | ggcaacaaat | cggccgtctt | tccctgcag | 120 |
| ctccttggct | tgatgtgga | tccaataaac | tctgtacagt | tttctaatca | tacaggatac | 180 |
| ccaacattta | gaggtcaggt | tcttaatggc | aaacagctct | gggaccttat | tgaaggactg | 240 |
| gaggaaaatc | agttgcttca | ttatacccat | ttattaacag | gttatatagg | ctcagtttcc | 300 |
| tttttagata | ctgtgctaca | agttgttgag | aaattgcgat | cagttaatcc | tgatcttgta | 360 |
| tatgttgtg | acccagttct | aggtgatgaa | ggaaaactat | atgttcctca | ggaggtaata | 420 |
| tctgtttatc | aacagaaggt | tgttccagtt | gcttcaatgc | ttacacctaa | ccaatttgaa | 480 |
| gttgaactac | ttactggatt | gaggatcacc | tccgaagaag | atggtttgac | agcttgtaat | 540 |
| accctccaca | gtgccggacc | acagaaggtg | gttataacta | gtgctcttat | tgaaggtaag | 600 |
| ctgctcctta | tcggaagtca | caaaaaaaca | gaggaacaac | agccagaaca | atttaagatt | 660 |
| gagataccaa | agatacctgc | atatttcacg | ggaactggag | atttgacaac | tgctctccta | 720 |
| ctaggatgga | gtaataaata | tcctgatagc | ctcgagaaag | cagcagaact | ggcagtttcc | 780 |
| agtttgcagg | cacttctgaa | agaactgtg | gaagactata | aaatggccgg | cttcgaccca | 840 |
| tcgaccagca | gcttagagat | ccggttgatc | caaagccagg | acgagatccg | aaacccaact | 900 |
| gttacatgca | aggctgtgaa | gtatggaagc | tga | | | 933 |

<210> SEQ ID NO 2
<211> LENGTH: 310
<212> TYPE: PRT
<213> ORGANISM: Zea mays

<400> SEQUENCE: 2

Met Ala Arg Pro Pro Ile Leu Ser Val Ala Leu Pro Ser Asp Thr Gly
 1               5                  10                  15

Arg Val Leu Ser Ile Gln Ser His Thr Val Gln Gly Tyr Val Gly Asn
            20                  25                  30

Lys Ser Ala Val Phe Pro Leu Gln Leu Leu Gly Phe Asp Val Asp Pro
        35                  40                  45

Ile Asn Ser Val Gln Phe Ser Asn His Thr Gly Tyr Pro Thr Phe Arg
    50                  55                  60

Gly Gln Val Leu Asn Gly Lys Gln Leu Trp Asp Leu Ile Glu Gly Leu
65                  70                  75                  80

Glu Glu Asn Gln Leu Leu His Tyr Thr His Leu Leu Thr Gly Tyr Ile
                85                  90                  95

Gly Ser Val Ser Phe Leu Asp Thr Val Leu Gln Val Val Glu Lys Leu
            100                 105                 110

Arg Ser Val Asn Pro Asp Leu Val Tyr Val Cys Asp Pro Val Leu Gly
        115                 120                 125

Asp Glu Gly Lys Leu Tyr Val Pro Gln Glu Val Ile Ser Val Tyr Gln
    130                 135                 140

```
Gln Lys Val Val Pro Val Ala Ser Met Leu Thr Pro Asn Gln Phe Glu
145                 150                 155                 160

Val Glu Leu Leu Thr Gly Leu Arg Ile Thr Ser Glu Glu Asp Gly Leu
                165                 170                 175

Thr Ala Cys Asn Thr Leu His Ser Ala Gly Pro Gln Lys Val Val Ile
            180                 185                 190

Thr Ser Ala Leu Ile Glu Gly Lys Leu Leu Leu Ile Gly Ser His Lys
        195                 200                 205

Lys Thr Glu Glu Gln Gln Pro Glu Gln Phe Lys Ile Glu Ile Pro Lys
    210                 215                 220

Ile Pro Ala Tyr Phe Thr Gly Thr Gly Asp Leu Thr Thr Ala Leu Leu
225                 230                 235                 240

Leu Gly Trp Ser Asn Lys Tyr Pro Asp Ser Leu Glu Lys Ala Ala Glu
                245                 250                 255

Leu Ala Val Ser Ser Leu Gln Ala Leu Leu Lys Arg Thr Val Glu Asp
            260                 265                 270

Tyr Lys Met Ala Gly Phe Asp Pro Ser Thr Ser Ser Leu Glu Ile Arg
        275                 280                 285

Leu Ile Gln Ser Gln Asp Glu Ile Arg Asn Pro Thr Val Thr Cys Lys
    290                 295                 300

Ala Val Lys Tyr Gly Ser
305                 310

<210> SEQ ID NO 3
<211> LENGTH: 413
<212> TYPE: DNA
<213> ORGANISM: Oryza sativa
<220> FEATURE:
<221> NAME/KEY: unsure
<222> LOCATION: (380)
<220> FEATURE:
<221> NAME/KEY: unsure
<222> LOCATION: (384)
<220> FEATURE:
<221> NAME/KEY: unsure
<222> LOCATION: (388)
<220> FEATURE:
<221> NAME/KEY: unsure
<222> LOCATION: (410)

<400> SEQUENCE: 3
gtttaaacaa gaagatggct tgaaagcttg caatgcgcta catagtgctg gaccgcgaaa      60
ggtggtaata actagtgcac ttattgaaga taagctgctc ctcattggaa gccacaaaaa     120
agcaaaggaa caaccaccag aacaatttaa gattgagata cccaagatac ctgcatattt     180
cacgggcact ggagatttaa caactgccct tctactagga tggagtaata ataccctga     240 taaccttgga gagggcgctg aactggcggt atccatttgc aaggcacccc taaggagaac     300
tgtggaagac tataaaagac tgggtttgac cctccaacca acacctagag atccgcctgg     360
attcaaaacc aaggatgaan tccnaagncc caagatacat gcaagctgtn aaa            413

<210> SEQ ID NO 4
<211> LENGTH: 136
<212> TYPE: PRT
<213> ORGANISM: Oryza sativa
<220> FEATURE:
<221> NAME/KEY: UNSURE
<222> LOCATION: (127)..(128)..(129)

<400> SEQUENCE: 4

Phe Lys Gln Glu Asp Gly Leu Lys Ala Cys Asn Ala Leu His Ser Ala
```

```
                1               5               10              15
         Gly Pro Arg Lys Val Val Ile Thr Ser Ala Leu Ile Glu Asp Lys Leu
                         20                  25                  30

Leu Leu Ile Gly Ser His Lys Lys Ala Lys Glu Gln Pro Pro Glu Gln
                     35                  40                  45

Phe Lys Ile Glu Ile Pro Lys Ile Pro Ala Tyr Phe Thr Gly Thr Gly
                 50                  55                  60

Asp Leu Thr Thr Ala Leu Leu Gly Trp Ser Asn Lys Tyr Pro Asp
             65                  70                  75              80

Asn Leu Gly Glu Gly Ala Glu Leu Ala Val Ser Ile Cys Lys Ala Pro
                         85                  90                  95

Leu Arg Arg Thr Val Glu Asp Tyr Lys Arg Leu Gly Leu Thr Leu Gln
                     100                 105                 110

Pro Thr Pro Arg Asp Pro Pro Gly Phe Lys Thr Lys Asp Glu Xaa Xaa
                     115                 120                 125

Xaa Pro Lys Ile His Ala Ser Cys
                 130                 135
```

<210> SEQ ID NO 5
<211> LENGTH: 812
<212> TYPE: DNA
<213> ORGANISM: Glycine max
<220> FEATURE:
<221> NAME/KEY: unsure
<222> LOCATION: (577)
<220> FEATURE:
<221> NAME/KEY: unsure
<222> LOCATION: (610)
<220> FEATURE:
<221> NAME/KEY: unsure
<222> LOCATION: (683)
<220> FEATURE:
<221> NAME/KEY: unsure
<222> LOCATION: (687)
<220> FEATURE:
<221> NAME/KEY: unsure
<222> LOCATION: (742)
<220> FEATURE:
<221> NAME/KEY: unsure
<222> LOCATION: (744)
<220> FEATURE:
<221> NAME/KEY: unsure
<222> LOCATION: (746)
<220> FEATURE:
<221> NAME/KEY: unsure
<222> LOCATION: (755)
<220> FEATURE:
<221> NAME/KEY: unsure
<222> LOCATION: (760)
<220> FEATURE:
<221> NAME/KEY: unsure
<222> LOCATION: (769)
<220> FEATURE:
<221> NAME/KEY: unsure
<222> LOCATION: (778)
<220> FEATURE:
<221> NAME/KEY: unsure
<222> LOCATION: (785)..(786)
<220> FEATURE:
<221> NAME/KEY: unsure
<222> LOCATION: (792)
<220> FEATURE:
<221> NAME/KEY: unsure
<222> LOCATION: (804)

<400> SEQUENCE: 5
gcacgaggag cattttccgg gcacgaaact cgaggaattc gcgcatggcg cctccaatcc     60
tctcgctcgc tcttccctcg aacaccggtc gagttctcag cattcaatct cacaccgttc    120

```
agggtatgt tggtaataaa tccgctgtct tccctctgca actactggga tatgatgtcg    180
atccaattaa ttccgtgcag ttttcgaatc atacaggata tccgacgttt aagggtcagg    240
ttttgaatgg acagcaactc tgggatctaa tcgaaggcct tgaaggaaat gatttattgt    300
tctatactca cttgctaaca ggttatattg gttcagagtc ttttctaaac actgtattgc    360
aagttgtcag caaacttcgg tcaacaaacc caggtctttc gtatgtatgt gatccagtga    420
tgggtgatga aggaaagctt tatgttcctc aagagctagt atcagtctat cgtgagaagg    480
ttgttccagt agcttcaatg ttgactccca accagtttga agcagaacta ctgacaggct    540
ttaggattca gtctgaagga catggccggg aggctgntag gcttctccat gcagctgggc    600
cttcaaaggn cataattaca agtataaata tagacgggat tcttctcctc attggcagtc    660
atccaaaaga aagggagag ccncccngac aatttaagat tgttattcca aaaataacca    720
gcttatttta cgggaacggg ananencatg actgnattcn tcttggttng agcataanta    780
cccannacaa ancttgagaa tgcngcggaa ct                                  812
```

<210> SEQ ID NO 6
<211> LENGTH: 196
<212> TYPE: PRT
<213> ORGANISM: Glycine max
<220> FEATURE:
<221> NAME/KEY: UNSURE
<222> LOCATION: (178)
<220> FEATURE:
<221> NAME/KEY: UNSURE
<222> LOCATION: (189)

<400> SEQUENCE: 6

```
Met Ala Pro Pro Ile Leu Ser Leu Ala Leu Pro Ser Asn Thr Gly Arg
  1               5                  10                  15

Val Leu Ser Ile Gln Ser His Thr Val Gln Gly Tyr Val Gly Asn Lys
                 20                  25                  30

Ser Ala Val Phe Pro Leu Gln Leu Leu Gly Tyr Asp Val Asp Pro Ile
             35                  40                  45

Asn Ser Val Gln Phe Ser Asn His Thr Gly Tyr Pro Thr Phe Lys Gly
         50                  55                  60

Gln Val Leu Asn Gly Gln Gln Leu Trp Asp Leu Ile Glu Gly Leu Glu
 65                  70                  75                  80

Gly Asn Asp Leu Leu Phe Tyr Thr His Leu Leu Thr Gly Tyr Ile Gly
                 85                  90                  95

Ser Glu Ser Phe Leu Asn Thr Val Leu Gln Val Val Ser Lys Leu Arg
            100                 105                 110

Ser Thr Asn Pro Gly Leu Ser Tyr Val Cys Asp Pro Val Met Gly Asp
        115                 120                 125

Glu Gly Lys Leu Tyr Val Pro Gln Glu Leu Val Ser Val Tyr Arg Glu
    130                 135                 140

Lys Val Val Pro Val Ala Ser Met Leu Thr Pro Asn Gln Phe Glu Ala
145                 150                 155                 160

Glu Leu Leu Thr Gly Phe Arg Ile Gln Ser Glu Gly His Gly Arg Glu
                165                 170                 175

Ala Xaa Arg Leu Leu His Ala Ala Gly Pro Ser Lys Xaa Ile Ile Thr
            180                 185                 190

Ser Ile Asn Ile
            195
```

<210> SEQ ID NO 7
<211> LENGTH: 773
<212> TYPE: DNA
<213> ORGANISM: Triticum aestivum

<400> SEQUENCE: 7

```
atggcgcggc cgccgatcct atccgtcgcg ctgccgtctg acaccggccg tgtgctcagc      60
atccagtccc acaccgtcca ggggtatgtt ggcaacaaat cggccgtctt tcccctgcag     120
ctccttggct tgatgtggga tccaataaac tctgtacagt tttctaatca tacaggatac     180
ccaacattta gagggtcagt tcttaatggc aaacagctct gggaacttat tgaaggactg     240
gaggaaaatc agctgcttca ttatacccat ttattaacag gttatatagg ctcagtttcc     300
tttttagata ctgtgctaca agttgttgag aaattgcgat cagttaatcc tgatcttgta     360
tatgtttgtg acccagttct aggtgatgaa ggaaaactat atgttcctca ggagctaata     420
tctgtttatc aacagaaggt tgttccagtt gcttcaatgc ttacacctaa ccaatttgaa     480
gttgaactac ttactggatt gaggatcacc tccgaagaag atggtttgac agcttgtaat     540
accctccaca gtgccggacc acagaaggtg gttataacta gtgctcttat tgaaggtaag     600
ctgctcctta tcggaagtca caaaaaaaca gaggaacaac agccagaaca atttaagatt     660
gagataccaa agatacctgc atatttcacg ggaactggag atttgacaac tgctctccta     720
ctaggatgga gtaataaata tcctgatatc ctcgaggggg ggccgtacca aat            773
```

<210> SEQ ID NO 8
<211> LENGTH: 256
<212> TYPE: PRT
<213> ORGANISM: Triticum aestivum

<400> SEQUENCE: 8

```
Met Ala Arg Pro Pro Ile Leu Ser Val Ala Leu Pro Ser Asp Thr Gly
 1               5                  10                  15

Arg Val Leu Ser Ile Gln Ser His Thr Val Gln Gly Tyr Val Gly Asn
            20                  25                  30

Lys Ser Ala Val Phe Pro Leu Gln Leu Leu Gly Phe Asp Val Asp Pro
        35                  40                  45

Ile Asn Ser Val Gln Phe Ser Asn His Thr Gly Tyr Pro Thr Phe Arg
    50                  55                  60

Gly Ser Val Leu Asn Gly Lys Gln Leu Trp Glu Leu Ile Glu Gly Leu
65                  70                  75                  80

Glu Glu Asn Gln Leu Leu His Tyr Thr His Leu Leu Thr Gly Tyr Ile
                85                  90                  95

Gly Ser Val Ser Phe Leu Asp Thr Val Leu Gln Val Val Glu Lys Leu
           100                 105                 110

Arg Ser Val Asn Pro Asp Leu Val Tyr Val Cys Asp Pro Val Leu Gly
       115                 120                 125

Asp Glu Gly Lys Leu Tyr Val Pro Gln Glu Leu Ile Ser Val Tyr Gln
   130                 135                 140

Gln Lys Val Val Pro Val Ala Ser Met Leu Thr Pro Asn Gln Phe Glu
145                 150                 155                 160

Val Glu Leu Leu Thr Gly Leu Arg Ile Thr Ser Glu Glu Asp Gly Leu
                165                 170                 175

Thr Ala Cys Asn Thr Leu His Ser Ala Gly Pro Gln Lys Val Val Ile
            180                 185                 190

Thr Ser Ala Leu Ile Glu Gly Lys Leu Leu Leu Ile Gly Ser His Lys
        195                 200                 205
```

```
Lys Thr Glu Glu Gln Gln Pro Glu Gln Phe Lys Ile Glu Ile Pro Lys
    210                 215                 220

Ile Pro Ala Tyr Phe Thr Gly Thr Gly Asp Leu Thr Thr Ala Leu Leu
225                 230                 235                 240

Leu Gly Trp Ser Asn Lys Tyr Pro Asp Ile Leu Glu Gly Gly Tyr Gln
                245                 250                 255
```

<210> SEQ ID NO 9
<211> LENGTH: 828
<212> TYPE: DNA
<213> ORGANISM: Zea mays
<220> FEATURE:
<221> NAME/KEY: unsure
<222> LOCATION: (74)

<400> SEQUENCE: 9

```
atgctggtgt cattgactgc acctaagctc tgtgcaaaaa agttcactgg cccacaccat      60
tttcttgggg gaangtttgt cccccccacct attttaaacc aattacggga cttcagctcc    120
tcctttaccc tgggcacatc aatgtgtgtg agaattggaa aagctccatc tgttgaaatt    180
tcatctctca gggagaacta tatttcccct gaacttcttg agagtcaagt gatgtctgat    240
ccatttgatc agttccttaa atggtttgat gaagcagtaa cagccggtcc cggtctgcgt    300
gagcccaatg caatggcttt gacaactgcc aacaaggaag gaaaaccttc ttcgaggatg    360
gttcttttaa agggagttga taaacaggga tttgtttggt atacaaatta tggtagccgg    420
aaggcgcatg acttgtgtga aaaccctaac gcagcactcc ttttctactg gaatgagatg    480
aaccgtcagg taagagttga agggtcagtt gagaaggttc cagaagctga atcagataaa    540
tatttccaca gccgcccacg tggaagtcag cttggtgcca tagtcagcaa gcagagtact    600
gtaattgctg aagagaagt tcttcaacag gattacaaga aattggaaca aaaatattct    660
gatgggagct tgattccaaa acctgaatat tggggtggct acaaaattga ccgacactt    720
tttgagttct ggcaaggaca acagtctcga ctgcatgacc ggttacaata ctcgcagaga    780
gaagtagatg ggagcacagt gtggcacatc gagaggttgt cccttga         828
```

<210> SEQ ID NO 10
<211> LENGTH: 275
<212> TYPE: PRT
<213> ORGANISM: Zea mays
<220> FEATURE:
<221> NAME/KEY: UNSURE
<222> LOCATION: (25)

<400> SEQUENCE: 10

```
Met Leu Val Ser Leu Thr Ala Pro Lys Leu Cys Ala Lys Lys Phe Thr
1               5                  10                  15

Gly Pro His His Phe Leu Gly Gly Xaa Phe Val Pro Pro Ile Leu
                20                  25                  30

Asn Gln Leu Arg Asp Phe Ser Ser Phe Thr Leu Gly Thr Ser Met
            35                  40                  45

Cys Val Arg Ile Gly Lys Ala Pro Ser Val Glu Ile Ser Ser Leu Arg
    50                  55                  60

Glu Asn Tyr Ile Ser Pro Glu Leu Leu Glu Ser Gln Val Met Ser Asp
65                  70                  75                  80

Pro Phe Asp Gln Phe Leu Lys Trp Phe Asp Glu Ala Val Thr Ala Gly
                85                  90                  95

Pro Gly Leu Arg Glu Pro Asn Ala Met Ala Leu Thr Thr Ala Asn Lys
```

```
                100             105             110
Glu Gly Lys Pro Ser Ser Arg Met Val Leu Lys Gly Val Asp Lys
            115                 120                 125

Gln Gly Phe Val Trp Tyr Thr Asn Tyr Gly Ser Arg Lys Ala His Asp
            130                 135                 140

Leu Cys Glu Asn Pro Asn Ala Ala Leu Leu Phe Tyr Trp Asn Glu Met
145                 150                 155                 160

Asn Arg Gln Val Arg Val Glu Gly Ser Val Lys Val Pro Glu Ala
            165                 170                 175

Glu Ser Asp Lys Tyr Phe His Ser Arg Pro Arg Gly Ser Gln Leu Gly
            180                 185                 190

Ala Ile Val Ser Lys Gln Ser Thr Val Ile Ala Gly Arg Glu Val Leu
            195                 200                 205

Gln Gln Asp Tyr Lys Lys Leu Glu Gln Lys Tyr Ser Asp Gly Ser Leu
            210                 215                 220

Ile Pro Lys Pro Glu Tyr Trp Gly Tyr Lys Leu Thr Pro Thr Leu
225                 230                 235                 240

Phe Glu Phe Trp Gln Gly Gln Gln Ser Arg Leu His Asp Arg Leu Gln
            245                 250                 255

Tyr Ser Gln Arg Glu Val Asp Gly Ser Thr Val Trp His Ile Glu Arg
            260                 265                 270

Leu Ser Pro
        275

<210> SEQ ID NO 11
<211> LENGTH: 555
<212> TYPE: DNA
<213> ORGANISM: Oryza sativa
<220> FEATURE:
<221> NAME/KEY: unsure
<222> LOCATION: (220)
<220> FEATURE:
<221> NAME/KEY: unsure
<222> LOCATION: (249)
<220> FEATURE:
<221> NAME/KEY: unsure
<222> LOCATION: (353)
<220> FEATURE:
<221> NAME/KEY: unsure
<222> LOCATION: (356)
<220> FEATURE:
<221> NAME/KEY: unsure
<222> LOCATION: (382)
<220> FEATURE:
<221> NAME/KEY: unsure
<222> LOCATION: (388)
<220> FEATURE:
<221> NAME/KEY: unsure
<222> LOCATION: (393)
<220> FEATURE:
<221> NAME/KEY: unsure
<222> LOCATION: (426)
<220> FEATURE:
<221> NAME/KEY: unsure
<222> LOCATION: (430)
<220> FEATURE:
<221> NAME/KEY: unsure
<222> LOCATION: (434)
<220> FEATURE:
<221> NAME/KEY: unsure
<222> LOCATION: (437)
<220> FEATURE:
<221> NAME/KEY: unsure
<222> LOCATION: (473)
<220> FEATURE:
<221> NAME/KEY: unsure
<222> LOCATION: (475)
```

<220> FEATURE:
<221> NAME/KEY: unsure
<222> LOCATION: (502)
<220> FEATURE:
<221> NAME/KEY: unsure
<222> LOCATION: (506)
<220> FEATURE:
<221> NAME/KEY: unsure
<222> LOCATION: (519)
<220> FEATURE:
<221> NAME/KEY: unsure
<222> LOCATION: (524)
<220> FEATURE:
<221> NAME/KEY: unsure
<222> LOCATION: (532)
<220> FEATURE:
<221> NAME/KEY: unsure
<222> LOCATION: (536)..(537)
<220> FEATURE:
<221> NAME/KEY: unsure
<222> LOCATION: (545)
<220> FEATURE:
<221> NAME/KEY: unsure
<222> LOCATION: (549)
<220> FEATURE:
<221> NAME/KEY: unsure
<222> LOCATION: (551)

<400> SEQUENCE: 11

```
atgctggtat cattgactgc accaaagctc tgtgcaaaaa aatttaccgg tccacaccat      60
tttcttgggg gtagatttgt tcccccacct attgtgagca aatataagct tcatcttcct     120
ccatatcccg gtacctcaat gtgtgtgaga attggaaaag ctccatctgt tgacatttca     180
tctctaagaa gaaattacat ctcccctgaa cttctcgagn aacaggtgat gcctgatcca     240
tttgataant tcgttagatg gtttgatgaa ctgttacgct ggctacgtga accaaatgct     300
atggttaaca actccgataa ggagggaaaa cttcgcaaag aatggccttt aanggngttg     360
ataaccacgg atttttgggg ancaattntg ganccaaaag gacatgatta cctgaaacca     420
aatgcngccn gttncantgg aaggaataac ggcagtaaaa taagtctgt canangtcca      480
gaaaagactg agatttcaaa cnccanagga ataacttgng aatntcacac angcanncat     540
ctganggant ncagg                                                      555
```

<210> SEQ ID NO 12
<211> LENGTH: 110
<212> TYPE: PRT
<213> ORGANISM: Oryza sativa
<220> FEATURE:
<221> NAME/KEY: UNSURE
<222> LOCATION: (74)
<220> FEATURE:
<221> NAME/KEY: UNSURE
<222> LOCATION: (83)

<400> SEQUENCE: 12

```
Met Leu Val Ser Leu Thr Ala Pro Lys Leu Cys Ala Lys Lys Phe Thr
 1               5                  10                  15

Gly Pro His His Phe Leu Gly Gly Arg Phe Val Pro Pro Ile Val
            20                  25                  30

Ser Lys Tyr Lys Leu His Leu Pro Pro Tyr Pro Gly Thr Ser Met Cys
        35                  40                  45

Val Arg Ile Gly Lys Ala Pro Ser Val Asp Ile Ser Ser Leu Arg Arg
    50                  55                  60

Asn Tyr Ile Ser Pro Glu Leu Leu Glu Xaa Gln Val Met Pro Asp Pro
65                  70                  75                  80
```

```
Phe Asp Xaa Phe Val Arg Trp Phe Asp Glu Leu Leu Arg Trp Leu Arg
             85                  90                  95
Glu Pro Asn Ala Met Val Asn Asn Ser Asp Lys Glu Gly Lys
         100                 105                 110
```

<210> SEQ ID NO 13
<211> LENGTH: 864
<212> TYPE: DNA
<213> ORGANISM: Glycine max

<400> SEQUENCE: 13

```
atgttgaaaa gggaagatgt tgatggtaca ggcattaaac ctgatatgtt ggtttctttg      60
acagccccaa gattaggtgc aaagaagttt ggtggtcctc accactttct aggaggtaga     120
tttgtcccac ctgctattgc agaaaaatat aagcttatac ttccaccata tcctggaact     180
tccatgtgtg ttcgaattgg aaggcctcca cgtattgata tctcagctct aagagagaac     240
tatatctctc cagaatttct tgaagagcag gtggaggctg acccttttaa tcagtttcat     300
aaatggttta atgatgcatt ggctgctggt ttgaaggaac aaatgctat gtccttgtca      360
actgtaggga aggacggaaa accctcatca gaatggtat tgctaaaagg cttggataag      420
gaaggatttg tgtggtacac aaactatgaa agtcgaaagg cacgtgaatt atctgaaaat     480
ccacgtgcat cacttctttt ttactgggat ggtttaaacc ggcaggtacg ggtggaaggg     540
cctgttcaga aagtctctga tgaggaatca gaacagtatt tccatagccg ccctagaggt     600
agtcagattg gagcaatagt cagcaagcag agtactgtag tgccgggtag gcatgttctt     660
tatcaggagt acaaagagct ggaagaaaaa tactctgatg gaagtttaat ccctaaacct     720
aagaactggg gtggatatag gctaacacca caacttttcg agttttggca agggcagaaa     780
tctcgcttgc atgacaggtt gcaatatact ccccatgaga tcaatggaca acggctgtgg     840
aaggttgacc ggttggctcc ttga                                            864
```

<210> SEQ ID NO 14
<211> LENGTH: 287
<212> TYPE: PRT
<213> ORGANISM: Glycine max

<400> SEQUENCE: 14

```
Met Leu Lys Arg Glu Asp Val Asp Gly Thr Gly Ile Lys Pro Asp Met
 1               5                  10                  15
Leu Val Ser Leu Thr Ala Pro Arg Leu Gly Ala Lys Lys Phe Gly Gly
             20                  25                  30
Pro His His Phe Leu Gly Gly Arg Phe Val Pro Pro Ala Ile Ala Glu
         35                  40                  45
Lys Tyr Lys Leu Ile Leu Pro Pro Tyr Pro Gly Thr Ser Met Cys Val
     50                  55                  60
Arg Ile Gly Arg Pro Pro Arg Ile Asp Ile Ser Ala Leu Arg Glu Asn
 65                  70                  75                  80
Tyr Ile Ser Pro Glu Phe Leu Glu Glu Gln Val Glu Ala Asp Pro Phe
             85                  90                  95
Asn Gln Phe His Lys Trp Phe Asn Asp Ala Leu Ala Ala Gly Leu Lys
         100                 105                 110
Glu Pro Asn Ala Met Ser Leu Ser Thr Val Gly Lys Asp Gly Lys Pro
     115                 120                 125
Ser Ser Arg Met Val Leu Leu Lys Gly Leu Asp Lys Glu Gly Phe Val
 130                 135                 140
```

```
Trp Tyr Thr Asn Tyr Glu Ser Arg Lys Ala Arg Glu Leu Ser Glu Asn
145                 150                 155                 160

Pro Arg Ala Ser Leu Leu Phe Tyr Trp Asp Gly Leu Asn Arg Gln Val
                165                 170                 175

Arg Val Glu Gly Pro Val Gln Lys Val Ser Asp Glu Ser Glu Gln
            180                 185                 190

Tyr Phe His Ser Arg Pro Arg Gly Ser Gln Ile Gly Ala Ile Val Ser
            195                 200                 205

Lys Gln Ser Thr Val Val Pro Gly Arg His Val Leu Tyr Gln Glu Tyr
            210                 215                 220

Lys Glu Leu Glu Glu Lys Tyr Ser Asp Gly Ser Leu Ile Pro Lys Pro
225                 230                 235                 240

Lys Asn Trp Gly Gly Tyr Arg Leu Thr Pro Gln Leu Phe Glu Phe Trp
                245                 250                 255

Gln Gly Gln Lys Ser Arg Leu His Asp Arg Leu Gln Tyr Thr Pro His
                260                 265                 270

Glu Ile Asn Gly Gln Arg Leu Trp Lys Val Asp Arg Leu Ala Pro
            275                 280                 285

<210> SEQ ID NO 15
<211> LENGTH: 456
<212> TYPE: DNA
<213> ORGANISM: Triticum aestivum

<400> SEQUENCE: 15
cacgaggata agcagggatt cgtttggtac acaaattacg gtagccaaaa agcacatgat    60
ttatcggaaa attcaaatgc ggcacttctt ttctactgga atgagatgaa ccgacaggtt   120
agagtagaag ggtcggttca gaaggtctca gaagaagaat ctgagaagta tttccacagc   180
cgcccacgtg gaagtcagct tggtgcaatt gttagcaagc agagcactgt catttcttga   240
agagaagttc tccaacaagc gtacaaggaa ttggagcaaa aatattctga cggtagcttc   300
atcccaaaac ccgattactg gggtggctac aagttgacac caaatctttt tgagttctgg   360
caaggccagc agtctcgtct gcatgaccgg ctacagtatt cacagcgaga attaggtggg   420
agtacagaat ggcacatcca aaggttgtcc ccttga                              456

<210> SEQ ID NO 16
<211> LENGTH: 150
<212> TYPE: PRT
<213> ORGANISM: Triticum aestivum

<400> SEQUENCE: 16

His Glu Asp Lys Gln Gly Phe Val Trp Tyr Thr Asn Tyr Gly Ser Gln
1               5                   10                  15

Lys Ala His Asp Leu Ser Glu Asn Ser Asn Ala Ala Leu Leu Phe Tyr
                20                  25                  30

Trp Asn Glu Met Asn Arg Gln Val Arg Val Glu Gly Ser Val Gln Lys
            35                  40                  45

Val Ser Glu Glu Glu Ser Glu Lys Tyr Phe His Ser Arg Pro Arg Gly
50                  55                  60

Ser Gln Leu Gly Ala Ile Val Ser Lys Gln Ser Thr Val Ile Ser Arg
65                  70                  75                  80

Glu Val Leu Gln Gln Ala Tyr Lys Glu Leu Glu Gln Lys Tyr Ser Asp
                85                  90                  95

Gly Ser Phe Ile Pro Lys Pro Asp Tyr Trp Gly Gly Tyr Lys Leu Thr
                100                 105                 110
```

-continued

```
Pro Asn Leu Phe Glu Phe Trp Gln Gly Gln Gln Ser Arg Leu His Asp
        115                 120                 125

Arg Leu Gln Tyr Ser Gln Arg Glu Leu Gly Gly Ser Thr Glu Trp His
        130                 135                 140

Ile Gln Arg Leu Ser Pro
145                 150
```

VITAMIN B METABOLISM PROTEINS

This application claims the benefit of U.S. Provisional Application No. 60/096,342, filed Aug. 12, 1998.

FIELD OF THE INVENTION

This invention is in the field of plant molecular biology. More specifically, this invention pertains to nucleic acid fragments encoding proteins involved in vitamin B6 metabolism in plants and seeds.

BACKGROUND OF THE INVENTION

Vitamins are organic nutrients required in small quantities for a variety of biochemical functions. Vitamins, generally, can not be synthesized by the body and must therefore be supplied by the diet. Besides being water soluble, vitamins in the B complex have little in common from the chemical point of view. Excess B vitamins are rarely accumulated or stored and thus must be provided regularly.

Vitamin B1 (thiamin) and vitamin B6 (pyridoxine, pyridoxal, and pyridoxamine) are essential for animal nutrition. Vitamin B6 consists of three closely related pyridine derivatives: pyridoxine, pyridoxal, and pyridoxamine. All forms of vitamin B6 are absorbed from the intestine, but some hydrolysis of the phosphate esters occurs during digestion. In the presence of magnesium ions and using ATP as a cofactor, pyridoxal kinase (EC 2.7.1.35) converts pyridoxine to pyridoxine 5'-phosphate. At least two pyridoxal kinases involved in the salvage pathway of vitamin B6 biosynthesis have been identified in *Escherichia coli* (Yang et al. (1998) *J. Bacteriol.* 180:1814–1821). Pyridoxine 5'-phosphate is converted to pyridoxal 5'-phosphate by the action of pyridoxamine 5'-phosphate oxidase (EC 1.4.3.5). Pyridoxal 5'-phosphate is the major form of B6 transported in plasma. Pyridoxal phosphate is used in transamination and is an integral part in the enzymes which breakdown glycogen. Studies in yeast and bacteria show that loss of function perturbs amino acid, fatty acid, and sterol metabolism (Lam, H. M. and Winkler, M. E. (1992) *Bacteriol.* 174:6033–6045; Zhao and Winkler (1995) *J. Bacteriol.* 177:883–891; Loubbardi et al. (1995) *J Bacteriol.* 177:1817–1823).

Thiamin and Vitamin B6 are present in almost all plant and animal tissues commonly used as foods, but the content is usually small. Accordingly, enzymes responsible for their biosynthesis are potential targets for future antibiotics, fungicides, and herbicides. Thus, a detailed understanding of the activation, structure, mechanism, kinetics, and substrate-binding properties of the vitamin B1 and vitamin B6 biosynthetic enzymes from plants (and other organisms) would aid in the rational design of chemical or other kinds of herbicides. Isolation and purification of the enzymes from plants would provide a valuable tool for the in vitro screening of inhibitors of vitamin B1 and vitamin B6 biosynthesis.

SUMMARY OF THE INVENTION

The instant invention relates to isolated nucleic acid fragments encoding enzymes involved in vitamin B6 metabolism. Specifically, this invention concerns an isolated nucleic acid fragment encoding a pyridoxal kinase or a pyridoxamine-phosphate oxidase and an isolated nucleic acid fragment that is substantially similar to an isolated nucleic acid fragment encoding a pyridoxal kinase or a pyridoxamine-phosphate oxidase. In addition, this invention relates to a nucleic acid fragment that is complementary to the nucleic acid fragment encoding pyridoxal kinase or pyridoxamine-phosphate oxidase.

An additional embodiment of the instant invention pertains to a polypeptide encoding all or a substantial portion of a vitamin B6 metabolic enzyme selected from the group consisting of pyridoxal kinase and pyridoxamine-phosphate oxidase.

In another embodiment, the instant invention relates to a chimeric gene encoding a pyridoxal kinase or a pyridoxamine-phosphate oxidase, or to a chimeric gene that comprises a nucleic acid fragment that is complementary to a nucleic acid fragment encoding a pyridoxal kinase or a pyridoxamine-phosphate oxidase, operably linked to suitable regulatory sequences, wherein expression of the chimeric gene results in production of levels of the encoded protein in a transformed host cell that is altered (i.e., increased or decreased) from the level produced in an untransformed host cell.

In a further embodiment, the instant invention concerns a transformed host cell comprising in its genome a chimeric gene encoding a pyridoxal kinase or a pyridoxamine-phosphate oxidase, operably linked to suitable regulatory sequences. Expression of the chimeric gene results in production of altered levels of the encoded protein in the transformed host cell. The transformed host cell can be of eukaryotic or prokaryotic origin, and include cells derived from higher plants and microorganisms. The invention also includes transformed plants that arise from transformed host cells of higher plants, and seeds derived from such transformed plants.

An additional embodiment of the instant invention concerns a method of altering the level of expression of a pyridoxal kinase or a pyridoxamine-phosphate oxidase in a transformed host cell comprising: a) transforming a host cell with a chimeric gene comprising a nucleic acid fragment encoding a pyridoxal kinase or a pyridoxamine-phosphate oxidase; and b) growing the transformed host cell under conditions that are suitable for expression of the chimeric gene wherein expression of the chimeric gene results in production of altered levels of pyridoxal kinase or pyridoxamine-phosphate oxidase in the transformed host cell.

An addition embodiment of the instant invention concerns a method for obtaining a nucleic acid fragment encoding all or a substantial portion of an amino acid sequence encoding a pyridoxal kinase or a pyridoxamine-phosphate oxidase.

A further embodiment of the instant invention is a method for evaluating at least one compound for its ability to inhibit the activity of a pyridoxal kinase or a pyridoxamine-phosphate oxidase, the method comprising the steps of: (a) transforming a host cell with a chimeric gene comprising a nucleic acid fragment encoding a pyridoxal kinase or a pyridoxamine-phosphate oxidase, operably linked to suitable regulatory sequences; (b) growing the transformed host cell under conditions that are suitable for expression of the chimeric gene wherein expression of the chimeric gene results in production of pyridoxal kinase or pyridoxamine-phosphate oxidase in the transformed host cell; (c) optionally purifying the pyridoxal kinase or the pyridoxamine-phosphate oxidase expressed by the transformed host cell; (d) treating the pyridoxal kinase or the pyridoxamine-phosphate oxidase with a compound to be tested; and (e) comparing the activity of the pyridoxal kinase or the pyridoxamine-phosphate oxidase that has been treated with a test compound to the activity of an untreated pyridoxal kinase or pyridoxamine-phosphate oxidase, thereby selecting compounds with potential for inhibitory activity.

BRIEF DESCRIPTION OF THE SEQUENCE LISTING

The invention can be more fully understood from the following detailed description and the accompanying Sequence Listing which form a part of this application.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821–1.825.

TABLE 1

Vitamin B6 Metabolic Enzymes

| | | SEQ ID NO: | |
|---|---|---|---|
| Protein | Clone Designation | (Nucleotide) | (Amino Acid) |
| Corn Pyridoxal Kinase | Contig of: cc1.mn0001.h9 cr1n.pk0161.c12 p0004.cb1hc14r p0038.crvae17r | 1 | 2 |
| Rice Pyridoxal Kinase | rlr6.pk0096.a8 | 3 | 4 |
| Soybean Pyridoxal Kinase | Contig of: sgc6c.pk001.o1 srm.pk0038.g4 | 5 | 6 |
| Wheat Pyridoxal Kinase | Contig of: wdk4c.pk006.119 wl1n.pk0106.e8 | 7 | 8 |
| Corn Pyridoxamine-Phosphate Oxidase | Contig of: cbn10.pk0048.g12 cpd1c.pk007.15 cr1n.pk0063.f3 csi1n.pk0050.f8 p0010.cbpcs54r p0072.comfr39r p0072.comfu19r | 9 | 10 |
| Rice Pyridoxamine-Phosphate Oxidase | Contig of: rlr48.pk0022.b10 rr1.pk097.c18 | 11 | 12 |
| Soybean Pyridoxamine-Phosphate Oxidase | Contig of: sfl1.pk0095.g3 sr1.pk0006.b5 | 13 | 14 |
| Wheat Pyridoxamine-Phosphate Oxidase | wr1.pk0018.f9 | 15 | 16 |

The Sequence Listing contains the one letter code for nucleotide sequence characters and the three letter codes for amino acids as defined in conformity with the IUPAC-IUBMB standards described in *Nucleic Acids Research* 13:3021–3030 (1985) and in the *Biochemical Journal* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, a "nucleic acid fragment" is a polymer of RNA or DNA that is single- or double-stranded, optionally containing synthetic, non-natural or altered nucleotide bases. A nucleic acid fragment in the form of a polymer of DNA may be comprised of one or more segments of cDNA, genomic DNA or synthetic DNA.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5%

SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Preferred are those nucleic acid fragments whose nucleotide sequences encode amino acid sequences that are 80% identical to the amino acid sequences reported herein. More preferred nucleic acid fragments encode amino acid sequences that are 90% identical to the amino acid sequences reported herein. Most preferred are nucleic acid fragments that encode amino acid sequences that are 95% identical to the amino acid sequences reported herein. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403–410; see also www.ncbi.nlm.nih.gov/BLAST/). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Molecular Biotechnology* 3:225).

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptide by the cell. "cDNA" refers to a double-stranded DNA that is complementary to and derived from mRNA. "Sense" RNA refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product(s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277) and particle-accelerated or "gene gun" transformation technology (Klein et al. (1987) *Nature* (London) 327:70–73; U.S. Pat. No. 4,945,050, incorporated herein by reference).

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

Nucleic acid fragments encoding at least a portion of several vitamin B6 metabolic enzymes have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other pyridoxal kinases or pyridoxamine-phosphate oxidases, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998–9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673–5677; Loh et al. (1989) *Science* 243:217–220). Products generated by the 3' and 5' RACE procedures can be combined to generate full-length cDNAs (Frohman and Martin (1989) *Techniques* 1:165).

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1; Maniatis).

The nucleic acid fragments of the instant invention may be used to create transgenic plants in which the disclosed polypeptides are present at higher or lower levels than normal or in cell types or developmental stages in which they are not normally found. This would have the effect of altering the level of active vitamin B1 or vitamin B6 in those cells.

Overexpression of the proteins of the instant invention may be accomplished by first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant chimeric gene can then be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J*. 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the chimeric gene described above may be further supplemented by altering the coding sequence to encode the instant polypeptides with appropriate intracellular targeting sequences such as transit sequences (Keegstra (1989) *Cell* 56:247–253), signal sequences or sequences encoding endoplasmic reticulum localization (Chrispeels (1991) *Ann. Rev. Plant Phys. Plant Mol. Biol.* 42:21–53), or nuclear localization signals (Raikhel (1992) *Plant Phys.* 100:1627–1632) added and/or with targeting sequences that are already present removed. While the references cited give examples of each of these, the list is not exhaustive and more targeting signals of utility may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds, and is not an inherent part of the invention. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

The instant polypeptides (or portions thereof) may be produced in heterologous host cells, particularly in the cells of microbial hosts, and can be used to prepare antibodies to the these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded vitamin B6 metabolic enzyme. An example of a vector for high level expression of the instant polypeptides in a bacterial host is provided (Example 7).

Additionally, the instant polypeptides can be used as a targets to facilitate design and/or identification of inhibitors of those enzymes that may be useful as herbicides. This is desirable because the polypeptides described herein catalyze various steps in vitamin B6 metabolism. Accordingly, inhibition of the activity of one or more of the enzymes described herein could lead to inhibition of plant growth. Thus, the instant polypeptides could be appropriate for new herbicide discovery and design.

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314–331).

The production and use of plant gene-derived probes for use in genetic mapping is described in Bematzky and Tanksley (1986) *Plant Mol. Biol. Reporter* 4(1):37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several to several hundred KB; see Laan et al. (1995) *Genome Research* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nature Genetics* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402–9406; Koes et al. (1995) *Proc. Natl. Acad. Sci USA* 92:8149–8153; Bensen et al. (1995) *Plant Cell* 7:75–84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries, Isolation and Sequencing of cDNA Clones cDNA libraries representing mRNAs from various corn, rice, soybean and wheat tissues were prepared. The characteristics of the libraries are described below.

Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651–1656). The resulting ESTs are analyzed using a Perkin Elmer Model 377 fluorescent sequencer.

Example 2

Identification of cDNA Clones cDNA clones encoding vitamin B6 metabolic enzymes were identified by conducting BLAST (Basic Local Align-

TABLE 2 cDNA Libraries from Corn, Rice, Soybean and Wheat

| Library | Tissue | Clone |
|---|---|---|
| cbn10 | Corn Developing Kernel (Embryo and Endosperm); 10 Days After Pollination | cbn10.pk0048.g12 |
| cc1 | Corn Undifferentiated Callus | cc1.mn0001.h9 |
| cpd1c | Corn Treated with Chemicals Related to Protein Kinases* | cpd1c.pk007.15 |
| cr1n | Corn Root From 7 Day Old Seedlings** | cr1n.pk0063.f3 cr1n.pk0161.c12 |
| csi1n | Corn Silk** | csi1n.pk0050.f8 |
| p0004 | Corn Immature Ear | p0004.cb1hc14r |
| p0010 | Corn Log Phase Suspension Cells Treated With A23187*** to Induce Mass Apoptosis | p0010.cbpcs54r |
| p0038 | Corn V5-Stage**** Roots | p0038.crvae17r |
| p0072 | Corn Mesocotyl 14 Days After Planting Etiolated Seedling | p0072.comfr39r p0072.comful 9r |
| rlr48 | Rice Leaf 15 Days After Germination, 48 Hours After Infection of Strain *Magaporthe grisea* 4360-R-62 (AVR2-YAMO); Resistant | rlr48.pk0022.b10 |
| rlr6 | Rice Leaf 15 Days After Germination, 6 Hours After Infection of Strain *Magaporthe grisea* 4360-R-62 (AVR2-YAMO); Resistant | rlr6.pk0096.a8 |
| rr1 | Rice Root of Two Week Old Developing Seedling | rr1.pk097.c18 |
| sfl1 | Soybean Immature Flower | sfl1.pk0095.g3 |
| sgc6c | Soybean Cotyledon 16–26 Days After Germination (all yellow) | sgc6c.pk001.o1 |
| sr1 | Soybean Root | sr1.pk0006.b5 |
| srm | Soybean Root Meristem | srm.pk0038.g4 |
| wdk4c | Wheat Developing Kernel, 21 Days After Anthesis | wdk4c.pk006.119 |
| wl1n | Wheat Leaf From 7 Day Old Seedling** | wl1n.pk0106.e8 |
| wr1 | Wheat Root From 7 Day Old Seedling | wr1.pk0018.f9 |

*Chemicals used included 1,2-didecanoyl rac glycerol, straurosporine, K-252, A3, H-7, olomoucine, rapamycin; which are commercially available from Calbiochem-Novabiochem Corp.
**These libraries were normalized essentially as described in U.S. Pat. No. 5,482,845, incorporated herein by reference.
***A23187 is commercially available from several vendors including Calbiochem.
****Corn developmental stages are explained in the publication "How a corn plant develops" from the Iowa State University Coop. Ext. Service Special Report No. 48 reprinted June 1993.

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, ment Search Tool; Altschul et al. (1993) *J. Mol. Biol.* 215:403–410; see also www.ncbi.nlm.nih.gov/BLAST/) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nature Genetics* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding Pyridoxal Kinase

The BLASTX search using the EST sequences from clones listed in Table 3 revealed similarity of the polypeptides encoded by the cDNAs to pyridoxal kinase from *Sus scrofa* and *Homo sapiens* (NCBI General Identifier Nos. 2773404 and 4505701, respectively). Shown in Table 3 are the BLAST results for individual ESTs ("EST"), or contigs assembled from two or more ESTs ("Contig"):

TABLE 3

BLAST Results for Sequences Encoding Polypeptides Homologous to Pyridoxal Kinase

| | | BLAST pLog Score | |
|---|---|---|---|
| Clone | Status | 2773404 | 4505701 |
| Contig of:<br>cc1.mn0001.h9<br>cr1n.pk0161.c12<br>p0004.cb1hc14r<br>p0038.crvae17r | Contig | 76.15 | 75.22 |
| rlr6.pk0096.a8 | EST | 11.10 | 12.00 |
| Contig of:<br>sgc6c.pk001.o1<br>srm.pk0038.g4 | Contig | 63.10 | 60.70 |
| Contig of:<br>wdk4c.pk006.119<br>wl1n.k0106.e8 | Contig | 65.52 | 65.40 |

The data in Table 4 represents a calculation of the percent identity of the amino acid sequences set forth in SEQ ID NOs:2, 4, 6 and 8 and the *Sus scrofa* and *Homo sapiens* (NCBI General Identifier Nos. 2773404 and 4505701, respectively).

TABLE 4

Percent Identity of Amino Acid Sequences Deduced From the Nucleotide Sequences of cDNA Clones Encoding Polypeptides Homologous to Pyridoxal Kinase

| | Percent Identity to | |
|---|---|---|
| SEQ ID NO. | 2773404 | 4505701 |
| 2 | 44.5 | 42.9 |
| 4 | 24.3 | 28.7 |
| 6 | 54.6 | 49.5 |
| 8 | 47.3 | 45.7 |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode an entire corn, and a substantial portion of a rice, a soybean and a wheat pyridoxal kinase. These sequences represent the first corn, rice, soybean and wheat sequences encoding pyridoxal kinase.

Example 4

Characterization of cDNA Clones Encoding Pyridoxamine-Phosphate Oxidase

The BLASTX search using the EST sequences from clones listed in Table 5 revealed similarity of the polypeptides encoded by the cDNAs to pyridoxamine-phosphate oxidase from Synechocystis sp., *Caenorhabditis elegans* and *Rattus norvegicus* (NCBI General Identifier Nos. 3122599, 3979940 and 3237304, respectively). Shown in Table 5 are the BLAST results for individual ESTs ("EST"), contigs assembled from the sequences of the entire cDNA inserts comprising the indicated cDNA clones and an EST ("Contig*"), or contigs assembled from two or more ESTs ("Contig"):

TABLE 5

BLAST Results for Sequences Encoding Polypeptides Homologous to Pyridoxamine-Phosphate Oxidase

| Clone | Status | NCBI General Identifier No. | BLAST pLog Score |
|---|---|---|---|
| Contig of:<br>cbn10.pk0048.g12<br>cpd1c.pk007.15<br>cr1n.pk0063.f3<br>csi1n.pk0050.f8<br>p0010.cbpcs54r<br>p0072.comfr39r<br>p0072.comfu19r | Contig | 3122599 | 55.10 |
| Contig of:<br>rlr48.pk0022.b10<br>rr1.pk097.c18 | Contig | 3979940 | 8.30 |

TABLE 5-continued

BLAST Results for Sequences Encoding Polypeptides Homologous to Pyridoxamine-Phosphate Oxidase

| Clone | Status | NCBI General Identifier No. | BLAST pLog Score |
|---|---|---|---|
| Contig of: sfl1.pk0095.g3:fis sr1.pk0006.b5 | Contig | 3237304 | 57.10 |
| wr1.pk0018.f9 | EST | 3237304 | 37.40 |

The data in Table 6 represents a calculation of the percent identity of the amino acid sequences set forth in SEQ ID NOs:10, 12, 14 and 16 and the *Rattus norvegicus* sequence (NCBI General Identifier No. 3237304).

TABLE 6

Percent Identity of Amino Acid Sequences Deduced From the Nucleotide Sequences of cDNA Clones Encoding Polypeptides Homologous to Pyridoxamine-Phosphate Oxidase

| SEQ ID NO. | Percent Identity to 3237304 |
|---|---|
| 10 | 38.3 |
| 12 | 14.5 |
| 14 | 40.2 |
| 16 | 45.3 |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a pyridoxamine-phosphate oxidase. These sequences represent the first corn, rice, soybean and wheat sequences encoding pyridoxamine-phosphate oxidase.

Example 5

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf (+) (Promega). Vector and insert DNA can be ligated at 15° C. overnight, essentially as described (Maniatis). The ligated DNA may then be used to transform *E. coli* XL1-Blue (*Epicurian Coli* XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al. (1987) *Nature* 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833–839).

Example 6

Expression of Chimeric Genes in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), SmaI, KpnI and XbaI. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embroys may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70–73, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810–812), the hygromycin phosphotransferase gene from plasmid pJR225 (from *E. coli*; Gritz et al.(1983) *Gene* 25:179–188) and the 3' region of the nopaline synthase gene from the T-DNA of the Ti plasmid of *Agrobacterium tumefaciens*. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μl spermidine (0.1 M), and 50 μL CaCl$_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 7

Expression of Chimeric Genes in Microbial Cells

The cDNAs encoding the instant polypeptides can be inserted into the T7 *E. coli* expression vector pBT430. This vector is a derivative of pET-3a (Rosenberg et al. (1987) *Gene* 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 µg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 µL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 µg/ml ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21(DE3) (Studier et al. (1986) *J. Mol. Biol.* 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 µL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One µg of protein from the soluble fraction of the culture can be separated by SDS-polyacrylamide gel electrophoresis. Gels can be observed for protein bands migrating at the expected molecular weight.

Example 8

Evaluating Compounds for Their Ability to Inhibit the Activity of Vitamin B6 Metabolic Enzymes The polypeptides described herein may be produced using any number of methods known to those skilled in the art. Such methods include, but are not limited to, expression in bacteria as described in Example 7, or expression in eukaryotic cell culture, in planta, and using viral expression systems in suitably infected organisms or cell lines. The instant polypeptides may be expressed either as mature forms of the proteins as observed in vivo or as fusion proteins by covalent attachment to a variety of enzymes, proteins or affinity tags. Common fusion protein partners include glutathione S-transferase ("GST"), thioredoxin ("Trx"), maltose binding protein, and C- and/or N-terminal hexahistidine polypeptide ("(His)$_6$"). The fusion proteins may be engineered with a protease recognition site at the fusion point so that fusion partners can be separated by protease digestion to yield intact mature enzyme. Examples of such proteases include thrombin, enterokinase and factor Xa. However, any protease can be used which specifically cleaves the peptide connecting the fusion protein and the enzyme.

Purification of the instant polypeptides, if desired, may utilize any number of separation technologies familiar to those skilled in the art of protein purification. Examples of such methods include, but are not limited to, homogenization, filtration, centrifugation, heat denaturation, ammonium sulfate precipitation, desalting, pH precipitation, ion exchange chromatography, hydrophobic interaction chromatography and affinity chromatography, wherein the affinity ligand represents a substrate, substrate analog or inhibitor. When the instant polypeptides are expressed as fusion proteins, the purification protocol may include the use of an affinity resin which is specific for the fusion protein tag attached to the expressed enzyme or an affinity resin containing ligands which are specific for the enzyme. For example, the instant polypeptides may be expressed as a fusion protein coupled to the C-terminus of thioredoxin. In addition, a (His)$_6$ peptide may be engineered into the N-terminus of the fused thioredoxin moiety to afford additional opportunities for affinity purification. Other suitable affinity resins could be synthesized by linking the appropriate ligands to any suitable resin such as Sepharose-4B. In an alternate embodiment, a thioredoxin fusion protein may be eluted using dithiothreitol; however, elution may be accomplished using other reagents which interact to displace the thioredoxin from the resin. These reagents include β-mercaptoethanol or other reduced thiol. The eluted fusion protein may be subjected to further purification by traditional means as stated above, if desired. Proteolytic cleavage of the thioredoxin fusion protein and the enzyme may be accomplished after the fusion protein is purified or while the protein is still bound to the ThioBond™ affinity resin or other resin.

Crude, partially purified or purified enzyme, either alone or as a fusion protein, may be utilized in assays for the evaluation of compounds for their ability to inhibit enzymatic activation of the instant polypeptides disclosed herein. Assays may be conducted under well known experimental conditions which permit optimal enzymatic activity. For example, assays for pyridoxal kinase and pyridoxamine-phosphate oxidase are presented by Merrill and Wang (1986) *Methods Enzymol.* 122:110–116.

What is claimed is:

1. An isolated polynucleotide that encodes a pyridoxal kinase, wherein the polypeptide has a sequence identity of at least 80%, based on the Clustal method of alignment, when compared to a polypeptide selected from the group consisting of SEQ ID NOs:2, 4, 6, and 8.

2. The polynucleotide of claim 1 wherein the sequence identity is at least 90%.

3. The polynucleotide of claim 1 wherein the sequence identity is at least 95%.

4. The polynucleotide of claim 1 wherein the polynucleotide encodes a polypeptide selected from the group consisting of SEQ ID NOs:2, 4, 6, and 8.

5. The polynucleotide of claim 1, wherein the polynucleotide comprises a nucleotide sequence selected from the group consisting of SEQ ID NOs:1, 3, 5, and 7.

6. An isolated complement of the polynucleotide of claim 1, wherein (a) the complement and the polynucleotide consist of the same number of nucleotides, and (b) the nucleotide sequences of the complement and the polynucleotide have 100% complementarity.

7. A chimeric gene comprising the polynucleotide of claim 1 operably linked to at least one regulatory sequence.

8. A cell comprising the polynucleotide of claim 1.

9. The cell of claim 8, wherein the cell is selected from the group consisting of a yeast cell, a bacterial cell and a plant cell.

10. A virus comprising the polynucleotide of claim 1.

11. A transgenic plant comprising the polynucleotide of claim 1.

12. A method for transforming a cell comprising introducing into a cell the polynucleotide of claim 11.

13. A method for producing a transgenic plant comprising (a) transforming a plant cell with the polynucleotide of claim 11, and (b) regenerating a plant from the transformed plant cell.

14. A vector comprising the polynucleotide of claim 1.

15. A seed comprising the chimeric gene of claim 7.

16. A method for isolating a polypeptide encoded by the polynucleotide of claim 1 comprising isolating the polypeptide from a cell transformed with said polynucleotide.

* * * * *